United States Patent
Nino et al.

(10) Patent No.: US 10,195,724 B2
(45) Date of Patent: *Feb. 5, 2019

(54) RATCHETING TORQUE WRENCH

(71) Applicant: ECA Medical Instruments, Newbury Park, CA (US)

(72) Inventors: John Nino, Simi Valley, CA (US); David Ivinson, Camarillo, CA (US)

(73) Assignee: ECA Medical Instruments, Thousand Oaks, CA (US)

( * ) Notice: Subject to any disclaimer, the term of this patent is extended or adjusted under 35 U.S.C. 154(b) by 192 days.

This patent is subject to a terminal disclaimer.

(21) Appl. No.: 15/239,685

(22) Filed: Aug. 17, 2016

(65) Prior Publication Data

US 2016/0354907 A1 Dec. 8, 2016

Related U.S. Application Data

(63) Continuation of application No. 14/837,523, filed on Aug. 27, 2015, now Pat. No. 9,446,507, which is a (Continued)

(51) Int. Cl.
*B25B 23/142* (2006.01)
*A61B 17/16* (2006.01)
(Continued)

(52) U.S. Cl.
CPC ...... *B25B 23/1427* (2013.01); *A61B 17/1624* (2013.01); *A61B 17/8875* (2013.01);
(Continued)

(58) Field of Classification Search
CPC . B25B 23/142; B25B 23/147; B25B 23/1427; B25B 13/46; B25B 13/461; A61B 17/1624; A61B 17/8875
See application file for complete search history.

(56) References Cited

U.S. PATENT DOCUMENTS 2,773,574 A  12/1956 Able et al.
3,742,787 A  7/1973 Whiteford
(Continued)

FOREIGN PATENT DOCUMENTS

EP  0287823 A1  10/1988
FR  2147674 A   3/1973
GB  2197609 A   5/1988

OTHER PUBLICATIONS

International Patent Application No. PCT/US2014/021755; Int'l Preliminary Report on Patentability; dated Sep. 24, 2015; 8 pages.
(Continued)

*Primary Examiner* — David B Thomas
(74) *Attorney, Agent, or Firm* — Baker & Hostetler LLP; Mark H. Krietzman

(57) ABSTRACT

A disposable ratcheting device and method is disclosed, which may include a shaft extending axially through at least a shank. The shank also provides a cup or chamber wherein a series of drive bodies reside in a movable fashion. The shank is placed in a body having an inner wall with teeth formed radially, The drive bodies have toes protruding beyond the shank and which, in a locked direction, engage the teeth inside the body.

14 Claims, 6 Drawing Sheets

Related U.S. Application Data continuation of application No. PCT/US2014/021755, filed on Mar. 7, 2014.

(60) Provisional application No. 61/777,765, filed on Mar. 12, 2013.

(51) Int. Cl.
  *A61B 17/88* (2006.01)
  *A61B 90/00* (2016.01)
  *B25B 15/04* (2006.01)
  *B25B 23/14* (2006.01)

(52) U.S. Cl.
  CPC .............. *A61B 90/03* (2016.02); *B25B 15/04* (2013.01); *B25B 23/141* (2013.01); *A61B 2090/031* (2016.02)

(56) References Cited

U.S. PATENT DOCUMENTS

| | | |
|---|---|---|
| 8,276,487 B2 | 10/2012 | Wengreen et al. |
| 9,445,873 B2* | 9/2016 | Nino .................. A61B 17/8883 |
| 9,446,507 B2* | 9/2016 | Nino .................. A61B 17/8875 |
| 9,475,178 B2* | 10/2016 | Pelletier ................ B25B 13/44 |
| 2005/0204868 A1 | 9/2005 | Liu |
| 2008/0087146 A1 | 4/2008 | Gao |
| 2008/0142329 A1 | 6/2008 | Kobayashi |
| 2009/0293683 A1 | 12/2009 | Chen |
| 2009/0293687 A1 | 12/2009 | Nino et al. |
| 2010/0326243 A1 | 12/2010 | Bouchard et al. |
| 2011/0094348 A1 | 4/2011 | Lee et al. |
| 2011/0094354 A1 | 4/2011 | Lai |
| 2012/0036968 A1 | 2/2012 | Lee |
| 2015/0202018 A1 | 7/2015 | Schaller et al. |
| 2016/0278748 A1* | 9/2016 | Nino ..................... A61B 17/00 |

OTHER PUBLICATIONS

European Patent Application No. 14778491 .2; Extended Search Report; dated Feb. 17, 2016; 9 pages.

International Search Report dated Aug. 27, 2014, issued in International patent application PCT/US2014/021755 filed Mar. 7, 2014.

* cited by examiner

RATCHETING TORQUE WRENCH

CROSS-REFERENCE TO RELATED APPLICATIONS

This patent application is a Continuation of U.S. Utility patent application Ser. No. 14/837,523 filed Aug. 27, 2014, which is a Continuation of International patent application PCT/US2014/021755 filed Mar. 7, 2014, which claims the full Paris Convention priority to, and benefit of U.S. Provisional patent application 61/777,765 filed Mar. 12, 2013 the disclosures of which are incorporated by reference as if fully set forth herein in their entirety.

BACKGROUND

1. Field

This disclosure relates to an inline disposable driver tool with plastic gear drive and, in particular, to a disposable medical use torque-limiting driver and ratchet that disengages at a predetermined torque limit.

2. General Background

Torque is a measure of force acting on an object that causes that object to rotate. In the case of a driver and a fastener, this measurement can be calculated mathematically in terms of the cross product of specific vectors:

$$\tau = r \times F$$

Where r is the vector representing the distance and direction from an axis of a fastener to a point where the force is applied and F is the force vector acting on the driver.

Torque has dimensions of force times distance and the SI unit of torque is the Newton meter (N–m). The joule, which is the SI unit for energy or work, is also defined as an N–m, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch-pounds.

Torque-limiting drivers are widely used throughout the medical industry. These torque-limiting drivers have a factory pre-set torque to ensure the accuracy and toughness required to meet a demanding surgical environment.

The medical industry has made use of both reusable and disposable torque-limiting drivers. In a surgical context, there is little room for error and these drivers must impart a precise amount of torque.

Reusable drivers require constant recalibration to ensure that the driver is imparting the precise amount of torque. Recalibration is a cumbersome task but must be done routinely. Such reusable devices also require sterilization.

Disposable drivers are an alternative to the reusable drivers. Once the driver has been used, it is discarded.

Disposable drivers are traditionally used for low torque applications. The standard torque values in these applications typically range from about 4 to about 20 inch-ounces. It has, however, been a challenge to develop a reliable disposable driver capable of imparting higher torques for larger applications.

Piecemeal drivetrain systems have been developed to gear-up or otherwise impart greater torque with disposable devices. Such piecemeal systems provide interchangeability of parts to a device, within which torque is transferred from part-to-part of a piecemeal system.

Ratchet is defined in Merriam-Webster dictionary as : a mechanism that consists of a bar or wheel having inclined teeth into which a pawl drops so that motion can be imparted to the wheel or bar, governed, or prevented and that is used in a hand tool (as a wrench or screwdriver) to allow effective motion in one direction only.

Ratcheting medical wrenches are known they are traditional metal catch and metal pawl to impart directional application of force.

DISCLOSURE

Briefly stated, torque devices according to implementations of the present disclosure obviate the shortfalls of piecemeal systems by reducing the number of part-to-part transitions of torque and ratcheting.

Disclosed in some exemplary implementations herein are aspects of a torque-limiting ratchet driver. The driver has a cylindrical body. It may have a handle affixed thereto. The body has an inner annular wall; an upper clutch shank with gear teeth on one side and an annular wall around the periphery on the opposite side forming the peripheral wall of drive body guides; a lower shank having a drive socket on one side and gear teeth on the opposing side; a nut; a spacer; a coil spring between the upper cylindrical shank and the ribbed nut, wherein the spring is configured to apply a force across the upper clutch shank and the lower shank; a shaft having a workpiece-engaging tip and a drive connection engaged within the drive socket of the lower cylindrical shank, the shaft extending axially through the lower shank, the upper clutch shank, and the spring and connected to the nut; a plurality of ratchet teeth formed or molded on the inner annular wall; one or more of movable drive bodies mounted to the upper clutch shank with a toe that protrudes through a passageway beyond the annular wall to engage a ratchet tooth when rotated in the positive lock direction; wherein the upper shank and the lower clutch shank engage for relative rotation, and wherein the upper clutch shank and the lower shank disengage when a predetermined torque limit is exceeded; and, wherein the upper shank and the lower clutch shank move in the reverse direction without imparting torque. In some instance when the plurality of movable drive bodies move in the unlocked direction they do not engage the ratchet teeth.

Disclosed in some exemplary implementations herein are aspects of a torque-limiting ratchet driver. The driver has a cylindrical body. It may have a handle affixed thereto. The body has an inner annular wall; an upper clutch shank with gear teeth on one side and an annular wall around the periphery on the opposite side forming the peripheral wall of drive body guides; a lower shank having a drive socket on one side and gear teeth on the opposing side; a nut; a spacer; a coil spring between the upper cylindrical shank and the ribbed nut, wherein the spring is configured to apply a force across the upper clutch shank and the lower shank; a shaft having a workpiece-engaging tip and a drive connection engaged within the drive socket of the lower cylindrical shank, the shaft extending axially through the lower shank, the upper clutch shank, and the spring and connected to the nut; a plurality of ratchet teeth formed or molded on the inner annular wall; one or more of movable drive bodies mounted to the upper clutch shank with a toe that protrudes through a passageway beyond the annular wall to engage a ratchet tooth when rotated in the positive lock direction; wherein the upper shank and the lower clutch shank engage for relative rotation, and wherein the upper clutch shank and the lower shank disengage when a predetermined torque limit is exceeded; wherein the upper shank and the lower clutch shank move in the reverse direction without imparting torque. In some instance the device further includes drive body guides; mounting posts within the drive body guides; a passageway fluidly connecting each drive body guide to the inner annular wall of the body; series of openings fluidly connecting drive body guides having mounting posts formed therein; and, whereby the toes protrude and may engage the ratchet teeth.

In some instance the above implementations may have drive body(s) which include a post guide that mates with the mounting post; a toe, instep ; a heel; flexible ankle; a first interior wall; and, wherein the flexible ankle flexes against the first interior wall during ratcheting to allow the body to rotate in the unlocked without imparting torque to the tip.

In some instance the above implementations may have drive body(s) which include a post guide that mates with the mounting post; a toe, instep; a heel; flexible ankle; a first interior wall; and, wherein each heel engages each of the second interior walls as bearing surfaces and locks the toes against the ratchet teeth.

Disclosed in some exemplary implementations herein are aspects of aplastic ratchet mechanism having a cylindrical body with a with an inner annular wall, a cylindrical end, and a cylindrical top; a plurality of ratchet teeth formed or molded on the inner annular wall; a cup shaped cylindrical upper shank (800) smaller than the interior diameter of the cylindrical body and having an annular wall around its periphery said annular wall forming the peripheral wall; drive body guides. In some instance the drive body guides have at least one passageway through the annular wall fluidly connecting each drive body guide to the inner annular wall of the body; at least one mounting post; one or more of movable drive bodies mounted to the cup shaped upper shank via the at least one mounting post; and, each drive body having a toe that protrudes through the passageway beyond the annular wall to engage a ratchet tooth when rotated in the positive lock direction.

Disclosed in some exemplary implementations herein are aspects of aplastic ratchet mechanism having a cylindrical body with a with an inner annular wall, a cylindrical end, and a cylindrical top; a plurality of ratchet teeth formed or molded on the inner annular wall; a cup shaped cylindrical upper shank smaller than the interior diameter of the cylindrical body and having an annular wall around its periphery said annular wall forming the peripheral wall; drive body guides. In some instance the drive body guides have at least one passageway through the annular wall fluidly connecting each drive body guide to the inner annular wall of the body; at least one mounting post; one or more of movable drive bodies mounted to the cup shaped upper shank via the at least one mounting post; and, each drive body having a toe that protrudes through the passageway beyond the annular wall to engage a ratchet tooth when rotated in the positive lock direction; each drive body further comprises: a post guide that mates with the mounting post; a toe, instep; a heel; and, flexible ankle.

In some instances a first interior wall; and, wherein the flexible ankle flexes against the first interior wall during ratcheting to allow the body to rotate in the unlocked without imparting rotation to the shank.

In some instances a first interior wall; and, wherein each heel engages each of the second interior walls as bearing surfaces and locks the toes against the ratchet teeth.

Disclosed in some exemplary implementations herein are aspects of aplastic ratchet mechanism having a cylindrical body with a with an inner annular wall, a cylindrical end, and a cylindrical top; a plurality of ratchet teeth formed or molded on the inner annular wall; a cup shaped cylindrical upper shank smaller than the interior diameter of the cylindrical body and having an annular wall around its periphery said annular wall forming the peripheral wall; drive body guides. In some instance the drive body guides have at least one passageway through the annular wall fluidly connecting each drive body guide to the inner annular wall of the body; at least one mounting post; one or more of movable drive bodies mounted to the cup shaped upper shank via the at least one mounting post; and, each drive body having a toe that protrudes through the passageway beyond the annular wall to engage a ratchet tooth when rotated in the positive lock direction; each drive body further comprises: a post guide that mates with the mounting post; a toe, instep; a heel; and, flexible ankle; a lower shank affixed to a shaft at its nose; a circumferential rim formed on the back side of the lower shank; and, a circumferential flange extending radially inward within the hollow of cylindrical body 6 forming a catch for the circumferential rim of the lower shank. In some instance the shaft is attached to a fastener Disclosed in some exemplary implementations herein are aspects of a plastic ratchet driving method to move a shaft. Placing within a hollow body having catches or teeth placed radially around an inner annular wall are a lower shank and and a cup shapedupper shank; affixed to the lower shank is a shaft with a tip at one end; placed within the body is a cup shaped upper shank; place within the cup shaped upper shank are a plurality of movable drive bodies each having a toe protruding radially from the shank towards the inner annular wall of the hollow body; and, connecting the toes to the teeth or catches around the inner annular wall rotating the shaft in a locked direction via rotating the body. In some instances rotating the body in an unlocked direction whereby the shaft does not rotate and the toes pass over the catches or teeth but do not engage. Rather the flexible ankles flex or bend and allow the drive body toe to pass over the catch without engagement. In some instances heels, flexible ankles, and an instep are formed on each drive body and each ankle flexes to allow the instep of the drive body to pass over the deflecting surface when rotating the body in an unlocked direction and the toes do not engage the bearing surface of the ratchet teeth. When rotated in a locking direction the instep of each drive body is placed under load via moving it against a bearing wall in the cup and each toe is also placed under load when it is moved against a bearing surface of a ratchet tooth.

Disclosed in some exemplary implementations herein are aspects of a disposable ratcheting device and method which includes at least a shaft extending axially through at least a shank. The shank also provides a cup or chamber wherein a series of drive bodies reside in a movable fashion. The shank is placed within a body having an inner wall with teeth formed radially, The drove bodies have flexible ankles on one side and toes on the other side. The toes protrude beyond the shank through passageways therein. When rotated in a locked direction the toes engage the teeth inside the body and impart rotation to the shaft. When rotated in an unlocked position the ankles flex allowing the toes to move over the teeth without engaging.

DRAWINGS

The above-mentioned features of the present disclosure will become more apparent with reference to the following description taken in conjunction with the accompanying drawings wherein like reference numerals denote like elements and in which.

Figure 1:
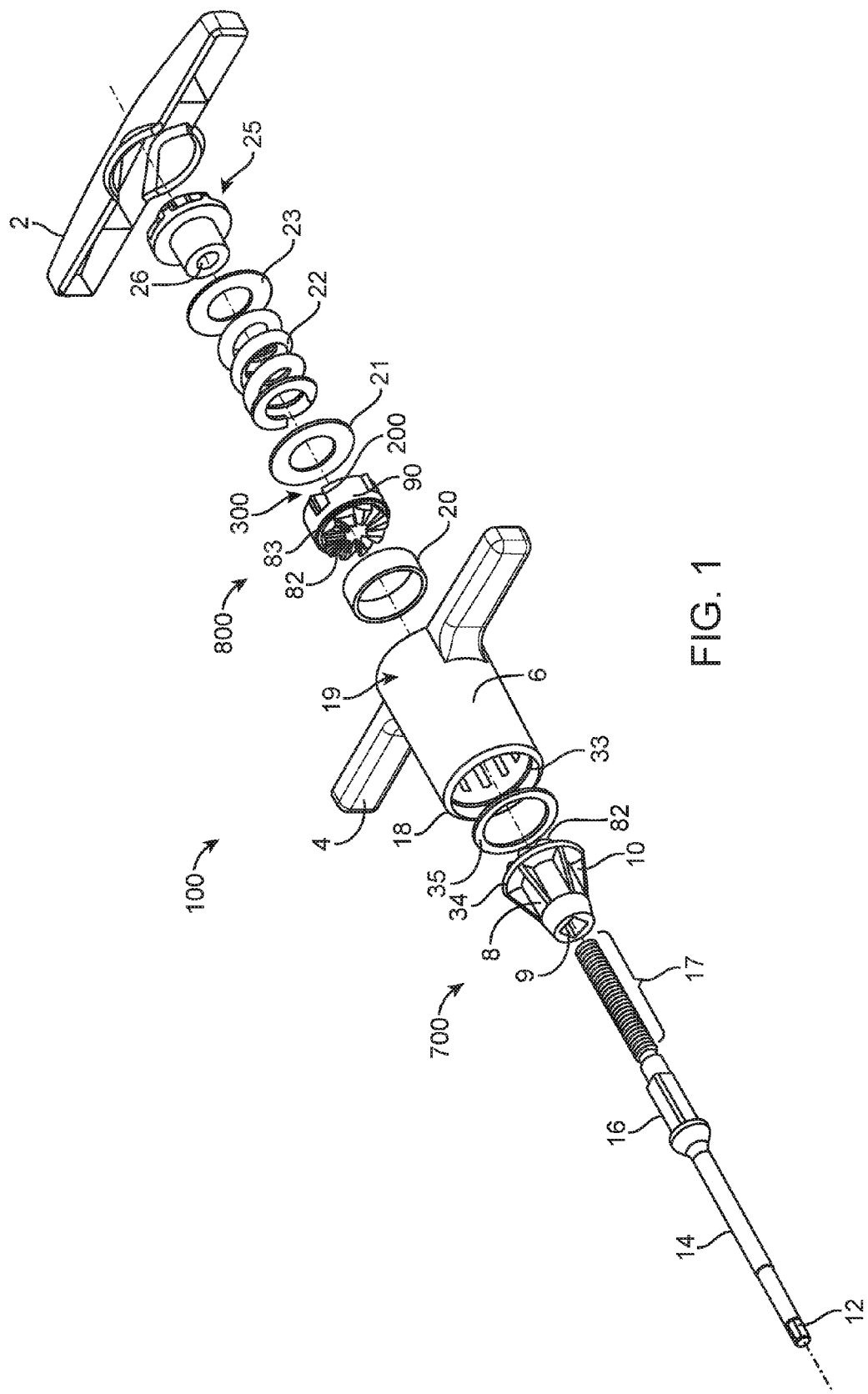
FIG. 1 shows an assembly view of some aspects of a torque limiting ratchet driver.

While the specification concludes with claims defining the features of the present disclosure that are regarded as novel, it is believed that the present disclosure's teachings will be better understood from a consideration of the following description in conjunction with the appendices, figures, in which like reference numerals are carried forward. All descriptions and callouts in the Figures are hereby incorporated by this reference as if fully set forth herein.

FURTHER DESCRIPTION

According to one or more exemplary implementations, as shown in FIGS. 1-5 torque-limiting ratcheting driver 100 are provided. Torque-limiting ratcheting driver 100 may have a generally T-shaped handle or other structure to facilitate use by a user. For example, the handle may by "T-shaped." The handle may include arms 4 at one end of an axially extending generally hollow cylindrical body 6. Cap 2 covers the same end of the handle. Cylindrical end 18 terminates cylindrical body 6 toward tip 12 of shaft 14. Cap 2 may be snap-fitted to cylindrical body 6, or may be welded, adhered, or attached by any equivalent thereof An exemplary implementation shows, at least in part, at cylindrical end 18, lower shank 700 provided, having an annularly tapering body and nose cone 8 along its length. Lower shank 700 may have a plurality of support flanges 10 that add strength while saving material. At one end, lower shank 700 tapers to drive socket 9 at the end of the nose cone 8 molded to engage drive connection 16 of shaft 14. An exemplary implementation shows, at least in part, shaft 14 provided, at one end, with work piece-engaging tip 12, adapted for engagement with an associated workpiece, such as a fastener or the like. The tip may also be a resector or other blade instrument. Work piece-engaging tip 12 is shown to be a socket wrench, but could be a screwdriver, wrench, or any other tool arrangement. During use as a torque limiting device the tip is connected to a fastener or the work piece. The tip can only be rotated by apply force visa vie rotating the body and the associated upper and lower shanks acting as a clutch within. During use as a ratchet only the device the tip is connected to a fastener or the work piece. The tip can only be rotated by apply force visa vie rotating the body and the associated ratcheting mechanism described below. At an opposite end, lower shank 700 has a plurality of gear 82 arranged in a crown gear formation 8, with circumferential rim 34 extending radially outward and an internal axial bore to accommodate at least a portion of shaft 14 extending there through.

According to aspects of one or more exemplary implementations, inside cylindrical body 6 a clutch and ratchet assembly is disposed. The clutch assembly includes upper clutch shank 800 for forcibly engaging lower shank 700. Upper clutch shank 800 has a bottom face that has a plurality of teeth 82 arranged in a crown gear formation around shaft guide 88 and a circumferential rim 83 extending radially outward and on the opposite side a plurality of drive body guides 202 each formed by an annular side wall 90, having passageways 200, a first interior wall 205 and second interior wall 207. The upper shank is cylindrical and of a size and shape to slide into the body 6 and rotate freely.

According to one or more exemplary implementations, upper clutch shank 800 includes at least a plurality of passageways 200 through the annular side wall 90 of the upper clutch shank through which drive body 300 may extend. The annular side wall 90 encircles the periphery of the upper clutch shank opposite the gear teeth and is the peripheral wall of each the drive body guide.

In assembly, drive connection 16 of shaft 14 is received into drive socket 9 of lower shank 700. Washer 35 maybe provided between circumferential rim 34 of lower shank 700 and circumferential flange 33 extending radially inward within the hollow of cylindrical body 6 forming a catch for the circumferential rim of the lower shank. Washer 35 may be of a polymer or other material having low coefficient of friction. Alternatively, circumferential rim 34 of lower shank 700 may be provided flush against circumferential flange 33 of cylindrical body 6. The opposite side of circumferential flange 33 receives circumferential rim 83 of upper clutch shank 800, allowing gear teeth 82 of lower shank 700 to engage gear teeth 82 of upper clutch shank 800 when a torque is applied.

Figure 2:
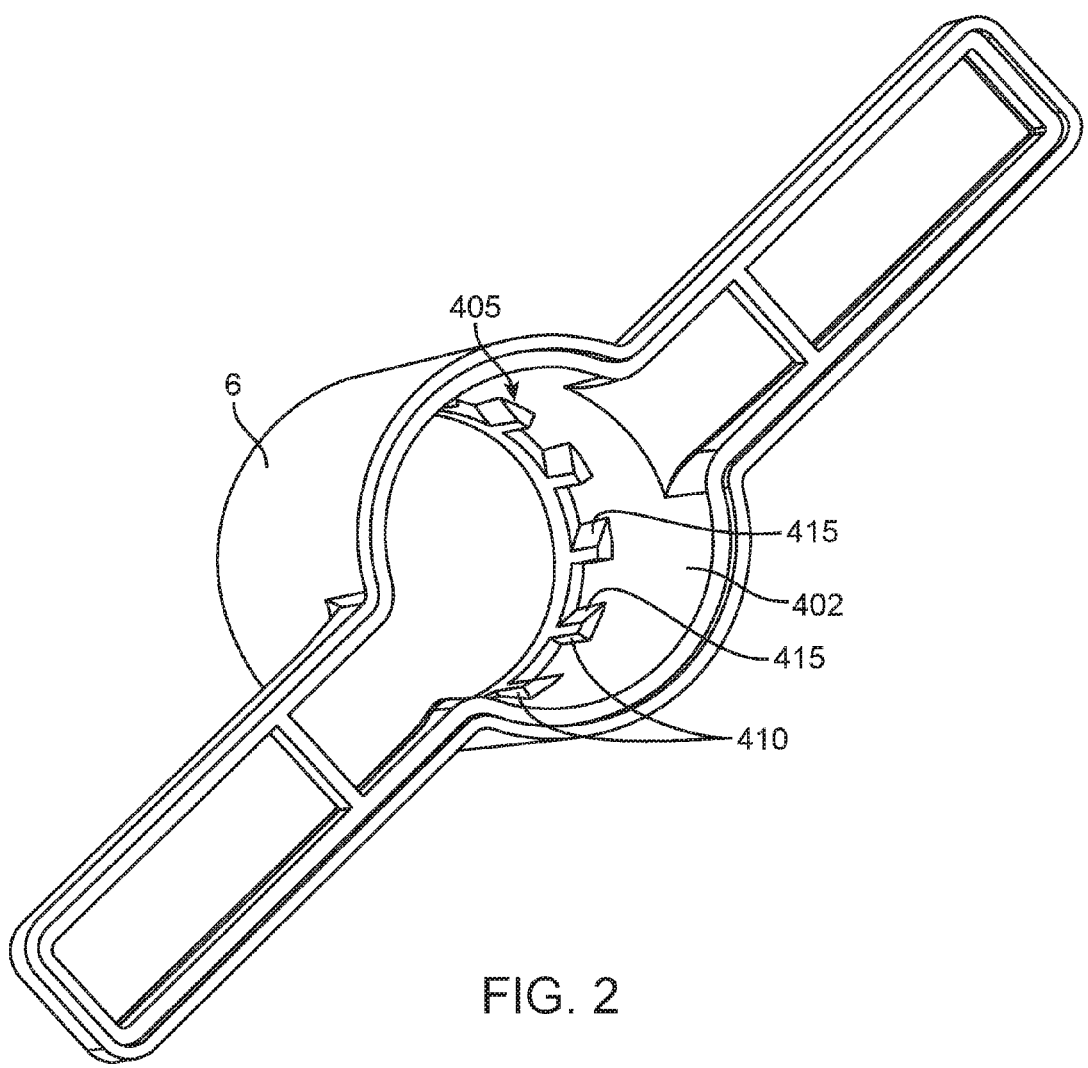
FIG. 2 shows the ratchet catch teeth inside a body.

FIG. 2 shows aspects of the inner annular wall of the body 6. Formed or molded as part of the inner annular wall 402 of the cylindrical body 6 are teeth 405 each protruding from the inner annular wall 402 4 inner. Each tooth has at least a bearing surface 410 and a deflecting surface 415. The deflecting surface of each tooth is angled in the same direction to form ramps from the inner annular wall 402 toward the bearing surface 410.

Figure 3A:
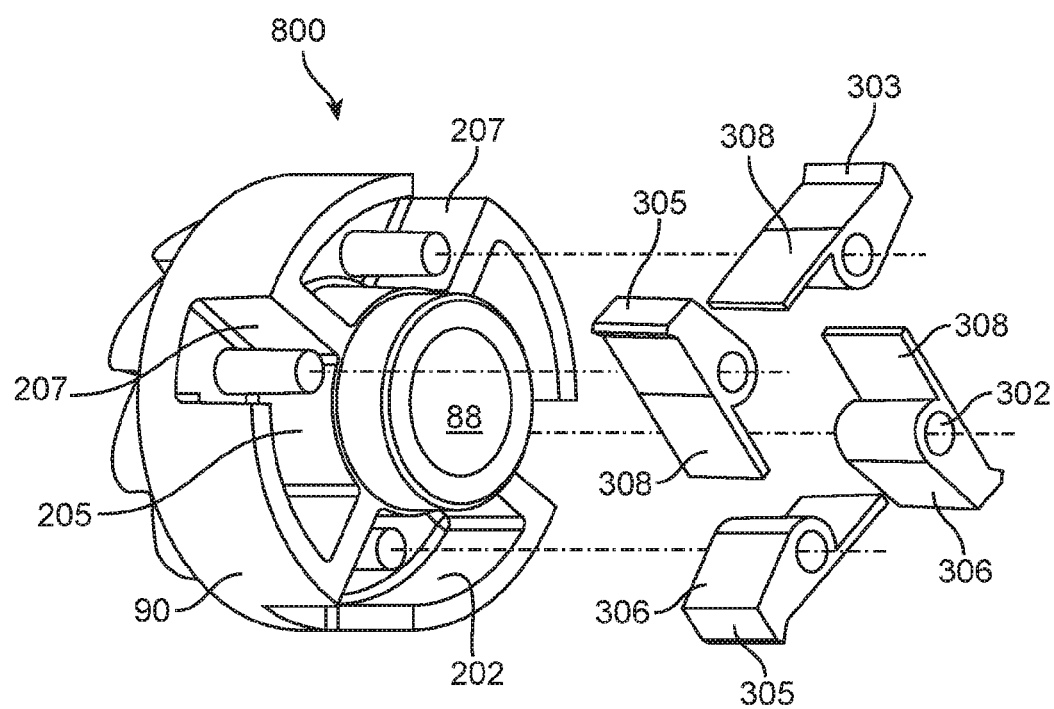
FIGS. 3A and 3B show assembly and assembled view of the ratchet drive fingers.
Figure 3B:
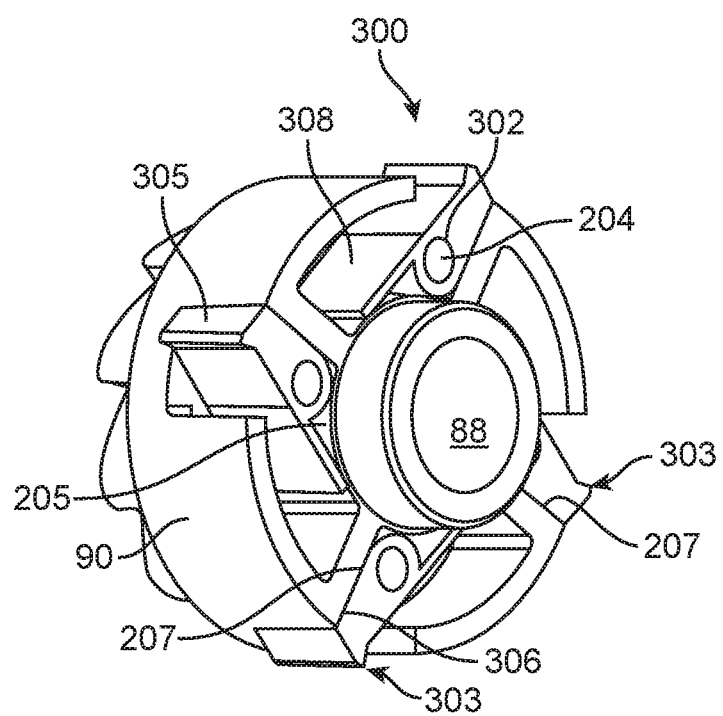
Figure 4:
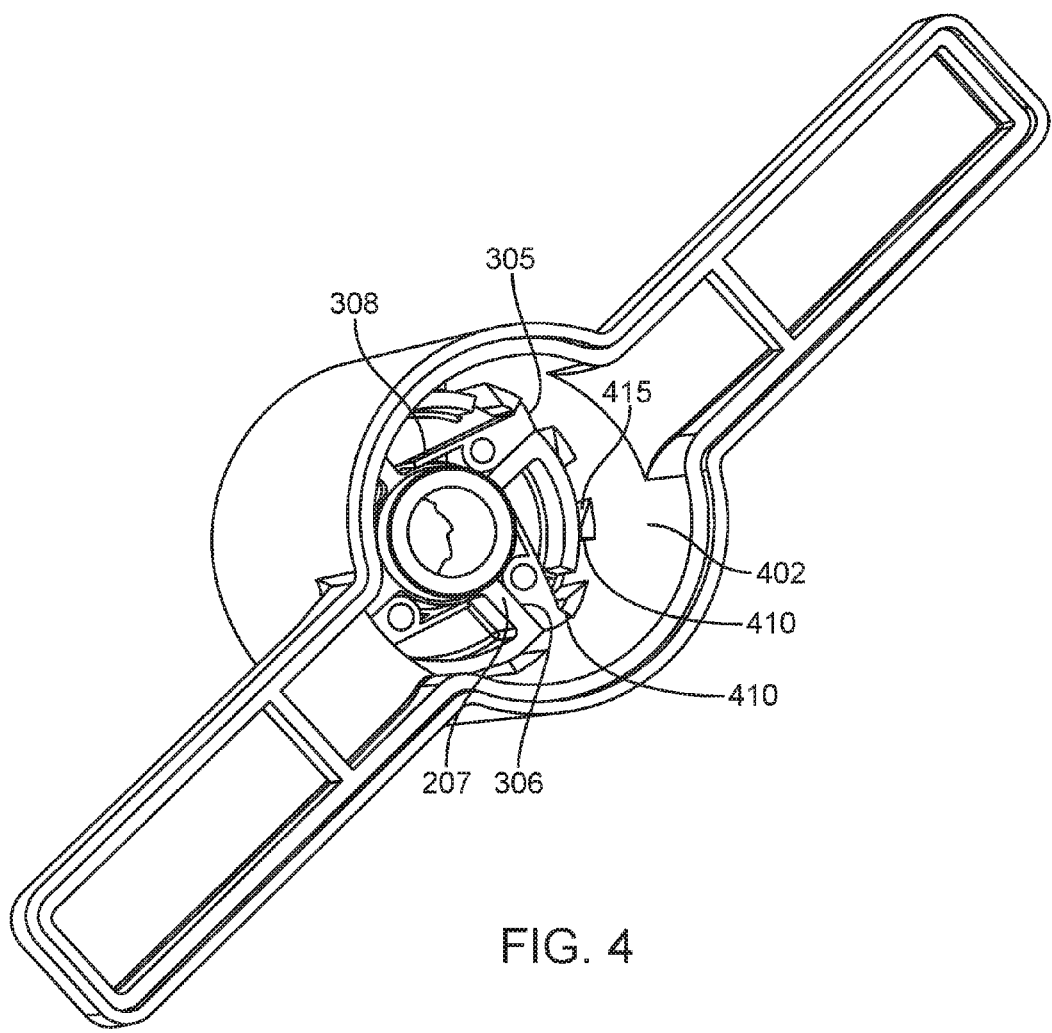
FIG. 4 shows a back to front view of the ratchet drive fingers mounted in the body.
Figure 5:
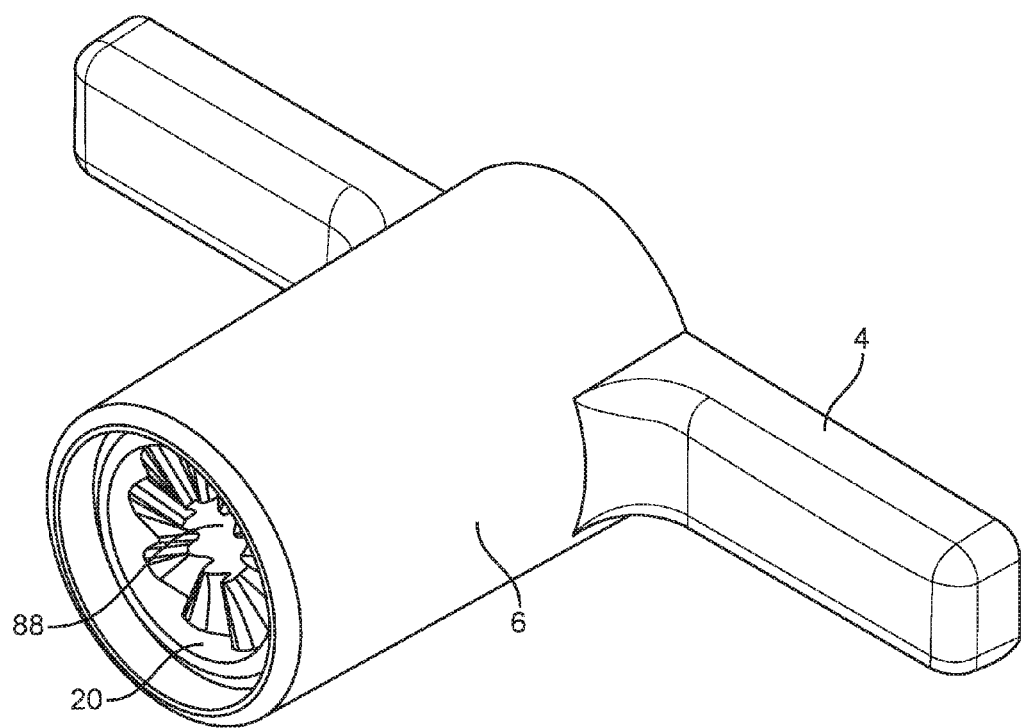
FIG. 5 shows a front to back view of the body with mounted upper clutch shank mechanism.

FIGS. 3A, 3B, and 4 show aspects of an upper clutch shank 800 exploded, assembled and mounted. The upper clutch shank 800 also forms the body of a ratchet device within the body 6. The upper clutch shank 800 has gear teeth 82 forming a spiral crown gear on one side and a cylindrical cup shape, with guide openings, on the other side formed by an annular side wall 90. The cup is a open chamber with additional openings in the annular wall to allow toes to protrude and move within. The annular wall has a series of openings fluidly connected to drive body guides 202 having mounting posts 204 formed therein. The drive body guides 202 open through passageways 200 in the annular side wall 90. Movably mated to each mounting post 204 is a drive body 300. Each drive body 300 is an elongated device divided roughly by a guide hole; it is multi-surfaced and each surface has a function. The posts guide 302 mates to the mounting posts 204 to movably attach the drive body 300. A toe 303 is at the most distal end of the drive body. An instep 305 is an angled wall adjacent to the toe. The heel 306 is a bearing surface adjacent to the instep 305. And an ankle 308 is on the opposite side of the post 204 then the toe. If the toe is at the distal end of the drive body the ankle is at the proximal end. The body guide is comprised of several walls which engage different portions of the drive body. In positive lock use as shown in FIG. 4, the toe 303 engages a bearing portion 410 of the ratchet tooth 405 and the heel 306 is a bearing surface against the second interior wall 207. In the unlocked state the instep engages the deflecting surface 415 and the ankle 308 is urged against a first interior wall 205, whereby the ankle 308 formed of a size and thickness to have a predetermined amount of flex allows the drive body to move from a first position with the heel 306 against the second interior wall 207, to a second position at least partially remote from the interior wall, thereby rotating around the mounting post 204. When the instep passes over the ratchet tooth 405, the flexible ankle 308 returns from the second position which is an under-load position, to the first at-rest position, thereby placing the toe in the proper orientation to engage a tooth's bearing surface 410 when the device is rotated in the locked direction, in this example indicated as a clockwise direction. The movable drive body or bodies in the cup shaped shank each have a toe 303 protruding radially from the shank towards the inner annular wall 402.

The drive bodies and drive body guides should be complementary size and shape. Those of ordinary skill in the art will recognize that it is within the scope of this disclosure that direction is a selectable feature and the ratchet teeth 405 may be reversed as well as the drive body guides 202. Moreover, the size and shape of the drive body, toe, ankle, instep and drive body guides may be varied.

Those of ordinary skill in the art will recognize that a disposable all-plastic ratchet is disclosed herein, the indication of its use with a torque limiting device is an exemplary implementation believed to be novel. The use of the ratcheting device with a non-torque limiting device is also within the scope of this disclosure. A non torque limiting device would be formed be permanently affixing the lower and upper shanks together thereby eliminating the gear 82 to gear 82 interaction and thereby providing a plastic disposable ratchet device to impart rotation to a shaft. One advantage of such a fixed torque configuration would be to allow removal of the spring 22 and supporting washers which add weight and cost. In such a configuration the shaft 14 is affixed in the nose 8 and the lower shank is inserted through cylindrical end 18 and the in the cylindrical body top 19 the upper shank is inserted. The lower and upper shanks are permanently affixed to one another yet remain rotatable within the body.

FIG. 2 shows ratchet teeth 405 oriented with the ramp function providing counterclockwise rotation of drive toe 305 whereby the toe does not engage the bearing surface 410 and therefore prevents a positive lock of the toe 303 at the bearing surface. Reversing the direction of both the deflecting surface would place the bearing surface in position for a positive lock in the counterclockwise direction if the drive bodies 300 were also mounted in a reverse orientation.

According to aspects of one or more exemplary implementations, force is applied across lower shank 700 and upper clutch shank 800 via the coil spring 22 within cylindrical body 6. Inside cylindrical body 6, shown in FIG. 1 spacer 20 and washer 21 are provided between upper clutch shank 800 and spring 22. Spacer 20 and washer 21 transfer pressure from spring 22 over the top face of upper shank 800. At an end of spring 22 opposite upper clutch shank 800, washer 23 and shoulder nut 25 hold spring 22 in a relatively compressed state. Washer 23 may be provided between nut 25 and spring 22 to facilitate relative rotation of nut 25 and spring 22. Nut 25 is formed of material softer than shaft 14, nut 25 has an unobstructed open center 26 with a diameter smaller than the diameter of shaft 14 and a smooth surface malleable enough to be deformed by the rotational insertion to said open center 26 of the threading 17 at an end of shaft 14.

According to one or more exemplary implementations, shaft 14 having threading 17 at an end opposite workpiece-engaging tip 12 engages a complementary threading within nut 25, thereby imparting pressure between the respective teeth 82 of lower shank 700 and upper clutch shank 800. Spring 22 and nut 25 provide the proper tensioning and biasing for the clutch assembly and, generally, the nut 25 is adjustable relative to shaft 14 to provide proper tension and calibration.

According to aspects of one or more exemplary implementations, various materials may be used for the components of driver 100. According to some exemplary implementations, at least one of body 6, nut 25, lower shank 700, and upper clutch shank 800 is of a plastic material or a composite including plastic. Plastic and other economical equivalents improve cost efficiency of production while providing high tensile strength, resistance to deformation, etc. Effective materials include plastics, resins, polymers, imides, fluoropolymers, thermoplastic polymers, thermosetting plastics, and the like as well as blends or mixtures thereof According to aspects of one or more exemplary implementations, at least one of lower shank 700 and upper shank 800 is of or includes at least one material that lubricous or otherwise reduces friction. The presence of a friction-reducing material allows geometric aspects of the engagement between lower shank 700 and upper shank 800 to govern whether teeth engage or disengage, thereby improving precision of the device.

According to aspects of one or more exemplary implementations, materials and components of drive 100 are resistant to sterilization, cleaning, and preparation operations. For example, drive 100 and parts thereof are configured to withstand sterilization by methods including radiation (e.g., gamma rays, electron beam processing), steam (e.g., autoclave), detergents, chemical (e.g., Ethylene Oxide), heat, pressure, inter alia. For example, materials for drive 100 may be selected according to resistance to one or more selected sterilization techniques.

According to aspects of one or more exemplary implementations, shaft 14 is of a rigid material. For example, shaft 14 may be of a metal, such as stainless steel. According to some exemplary implementations, high torque capabilities of drive 100 are, at least in part, provided by features that maintain an effective engagement between drive connection 16 of shaft 14 and drive socket 9 of lower shank 700. For example, some exemplary implementations are provided to improve the ability of drive 100 to maintain its grip on shaft 14 up to a greater range of torque.

According to aspects of one or more exemplary implementations, a single integrated shaft 14 spans the distance between workpiece-engaging tip 12 and an engagement point with nut 25. This configuration enables greater torque capabilities than a piecemeal or fragmented set of interconnected components. This reduces the number of interconnections between a source of a torque and a location to which the torque is transferred.

According to one or more exemplary implementations, shaft 14 having drive connection 16 between opposing extensions stabilizes drive connection 16 within drive socket 9. Placement of drive connection 16 at a medial segment of shaft 14—rather than at an end thereof—facilitates a more stable engagement between drive connection 16 and drive socket 9, thereby increasing the ability of engagement to transfer high amounts of torque.

According to one or more exemplary implementations, an engagement of drive connection 16 within drive socket 9 is maintained by the connection of the integrated portion of shaft 14 that extends to nut 25. According to some exemplary implementations, both threading 17 and drive connection 16 are of a single integrated structure (i.e., shaft 14). A force applied by spring 22 to nut 25 is directly transferred along shaft 14 from threading 17 to drive connection 16. This force securely maintains drive connection 16 within drive socket 9. This engagement enables transfers of greater amounts of torque from lower shank 700 (i.e., via drive socket 9) to shaft 14 (i.e., via drive connection 16).

According to aspects of some exemplary implementations, drive connection 16 and drive socket 9 have complementary geometries. One or more of a variety of configurations may be provided for engaging drive connection 16 within drive socket 9. For example drives and associated connections may include triangular, square, hexagonal, rectangular, etc. According to aspects of one or more exemplary implementations, a substantially square drive connection 16 and drive socket 9 provide high torque transfer capabilities. Out of a variety of drive types, experimental results demonstrated that square drives and connections were among the most successful at transferring high torque without failure. Drive connection 16 and drive socket 9 may have rounded corners and edges to reduce or distribute stress risers.

According to aspects of one or more exemplary implementations, driver 100 capable of transferring higher torque may be provided with spring 22 having a greater spring constant (i.e., force constant) or otherwise be calibrated with spring 22 exerting greater forces in an initial (rest) state. A more robust spring 22 increases the probability of a friction grip relative to washer 21. Provision of additional spacer 20 provides counter clockwise rotation without increasing spring tension when the drive toes are disengaged from the load bearing surface 410.

According to aspects of one or more exemplary implementations, the plurality of teeth 82 are formed on the top face of lower shank 700 and the bottom face of upper clutch shank 800 to forcibly engage to impart torque from the handle to the workpiece when a torque is applied.

According to aspects of one or more exemplary implementations, teeth 82 are circumferentially spaced in a crown gear formation of the top face and bottom face of lower shank 700 and upper clutch shank 800, respectively. Teeth 82 are preferably configured in a spiral formation. Each face of lower shank 700 and upper clutch shank 800 has an inner radius and an outer radius and teeth 82 spiral around the inner radius resulting in a larger tooth detail when viewing the tooth from the outer radius relative to the tooth detail when viewing the tooth from the inner radius. The spiral configuration of teeth 82 can also be defined as having a longer inclined face 66 at the edge of the tooth on or near the outer radius relative to inclined face 66 at the edge of the tooth on or near the inner radius of lower shank 700 and upper shank 800. Results have shown that teeth arranged in said spiral configuration provide an increased reliability and/or precision in torque consistency when compared to non-spiral counterparts.

According to aspects of one or more exemplary implementations, the extent to which threading 17 of shaft 14 is threaded into nut 25 controls the amount of compression or preload on spring 22 which, subsequently, controls the limiting torque required to effect relative rotation of lower shank 700 and upper clutch shank 800. If shaft 14 is more deeply threaded into nut 25, then a higher torque will be required to disengage teeth 82 of lower shank 700 and upper clutch shank 800. If shaft 14 is less deeply threaded into nut 25, then a lower torque will be required. Accordingly, a predetermined torque limit is selectively programmable. The predetermined torque limit may correspond to a predefined threshold of a workpiece (e.g., a fastener) having a desired level of torque-based installation not to be exceeded.

When a force beyond the predetermined torque limit is achieved, teeth 82 of lower shank 700 and upper shank 800 will continue to disengage, resulting in rotation of the handle with no further rotation of workpiece-engaging tip 12. Thus, the handle will continue to rotate, disengaging teeth 82 with every rotational movement that will not impart continued force beyond a predefined threshold to the fastener.

According to aspects of one or more exemplary implementations, the disposable torque-limiting ratchet driver of the present disclosure is capable of imparting torques of up to about 120 inch-pounds. For example, the torque output range may be selected between about 70 inch-pounds and about 120 inch-pounds. Typically, the torque requirement is different for different operations and for different implants. For example, applications may include those in the field of orthopedic surgery, construction and emplacement of implants, etc. Therefore, in some instances, the predetermined torque limits maybe at least about 1 inch-pound. In other instances, the predetermined torque limit may be between about 5 inch-pounds and about 150 inch-pounds, depending on an implant's specifications. In other instances, the predetermined torque limit may be between about 70 inch-pounds and about 120 inch-pounds, depending on an implant's specifications.

In some instances, the driver 100 may be prepackaged with an implant provided for one-time use. Such a methodology matches the driver that will impart a required amount of torque with the implant.

In other instances, the driver 100 may be reusable. Shaft 14 may be interchangeably fixed relative to nose cone 8 for the accommodation of multiple workpiece-engaging tips 12. It is also to be appreciated that the handle of the driver is not limited to a T-shape and may be provided in any other suitable configuration.

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising," are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A plastic ratchet mechanism, comprising:
    a cylindrical body with a with an inner annular wall, a cylindrical end (18), and a cylindrical top (19);
    a plurality of ratchet teeth formed or molded on the inner annular wall;
    a cup shaped cylindrical upper shank smaller than the interior diameter of the cylindrical body and having an annular wall around its periphery said annular wall forming the peripheral wall;
    drive body guides comprising:
    at least one passageway through the annular wall fluidly connecting each drive body guide to the inner annular wall of the body;
    at least one mounting post;
    one or more of movable drive bodies mounted to the cup shaped upper shank via the at least one mounting post; and,
    each drive body having a toe that protrudes through the passageway beyond the annular wall to engage a ratchet tooth when rotated in the positive lock direction.

2. The plastic ratchet mechanism of claim 1 wherein each drive body further comprises:
    a post guide that mates with the mounting post;
    a toe, instep;
    a heel; and,
    flexible ankle.

3. The plastic ratchet mechanism of claim 2 further comprising:
    a first interior wall; and,
    wherein the flexible ankle flexes against the first interior wall during ratcheting to allow the body to rotate in the unlocked without imparting rotation to the shank.

4. The plastic ratchet mechanism of claim 3 further comprising:
    a lower shank affixed to a shaft at its nose;
    a circumferential rim formed on the back side of the lower shank; and,
    a circumferential flange extending radially inward within the hollow of cylindrical body forming a catch for the circumferential rim of the lower shank; and,
    wherein the shaft is attached to a fastener.

5. The plastic ratchet mechanism of claim 2 further comprising:
    a first interior wall; and,
    wherein each heel engages each of the second interior walls as bearing surfaces and locks the toes against a bearing surface (410) of each ratchet teeth.

6. The plastic ratchet mechanism of claim 5 further comprising:
    a lower shank affixed to a shaft at its nose;
    a circumferential rim formed on the back side of the lower shank; and,
    a circumferential flange extending radially inward within the hollow of cylindrical body forming a catch for the circumferential rim of the lower shank; and,
    wherein the shaft is attached to a fastener.

7. The plastic ratchet mechanism of claim 2 further comprising:
    a second interior wall; and,
    wherein each ankle flexes against each of the first interior walls and the insteps pass over the deflecting surfaces (415) of each ratchet tooth.

8. The plastic ratchet mechanism of claim 7 wherein the shaft is attached to a fastener.

9. The plastic ratchet mechanism of claim 1 further comprising:
    a lower shank affixed to a shaft at its nose;
    a circumferential rim (34) formed on the back side of the lower shank; and,
    a circumferential flange (33) extending radially inward within the hollow of cylindrical body 6 forming a catch for the circumferential rim of the lower shank.

10. A method of ratchet driving a shaft, the method comprising:
- Within a hollow body placing a lower shank and an upper shank;
- forming a plurality of ratchet teeth on the inner annular wall of the hollow body;
- affixing a shaft with a tip at one end to a cup shaped upper shank;
- placing the cup shaped upper shank within the hollow body;
- placing a plurality of movable drive bodies in the cup shaped shank and each drive body having a toe protruding radially from the shank towards the inner annular wall of the hollow body; and,
- connecting the toes to the ratchet teeth via rotating the shaft in a locked direction when rotating the body.

11. The method of ratchet driving a shaft of claim 10 the method further comprising affixing the shaft to a fastener or resector.

12. The method of ratchet driving a shaft of claim 10 the method further comprising rotating the body in an unlocked direction whereby the toes disengage from the ratchet teeth and the shaft does not rotate.

13. The method of ratchet driving a shaft of claim 12 the method further comprising:
- forming heels, flexible ankles, and an instep on each drive body; and,
- flexing each ankle when the instep of the drive body passes over the deflecting surface of ratchet tooth whereby the toe does not engage a ratchet tooth.

14. The method of ratchet driving a shaft of claim 10 the method further comprising:
- forming heels, flexible ankles, and an instep on each drive body; and,
- placing the instep under load by moving it against a bearing wall in the cup and placing each toe against a bearing surface of a ratchet tooth.

* * * * *